United States Patent
Lim et al.

(10) Patent No.: US 7,808,629 B2
(45) Date of Patent: Oct. 5, 2010

(54) METHODS, ASSEMBLIES AND SYSTEMS FOR INSPECTING A PHOTOMASK

(75) Inventors: Kwon Lim, Hwaseong-si (KR); Do-young Kim, Daejeon (KR)

(73) Assignee: Samsung Electronics Co., Ltd. (KR)

( * ) Notice: Subject to any disclaimer, the term of this patent is extended or adjusted under 35 U.S.C. 154(b) by 362 days.

(21) Appl. No.: 11/865,145

(22) Filed: Oct. 1, 2007

(65) Prior Publication Data
US 2008/0079931 A1 Apr. 3, 2008

(30) Foreign Application Priority Data
Oct. 2, 2006 (KR) .................. 10-2006-0097150

(51) Int. Cl.
*G01N 21/00* (2006.01)
(52) U.S. Cl. .............. 356/237.5; 356/237.4; 356/237.2
(58) Field of Classification Search .............. None
See application file for complete search history.

(56) References Cited

U.S. PATENT DOCUMENTS 6,297,879 B1 * 10/2001 Yang et al. .............. 356/237.5
6,407,373 B1 * 6/2002 Dotan ..................... 250/201.3
7,187,436 B2 * 3/2007 Harding et al. .......... 356/237.2

FOREIGN PATENT DOCUMENTS

| JP | 6110969 | 4/1994 |
|----|---------|--------|
| JP | 7092094 | 4/1995 |
| JP | 2000019718 | 1/2000 |
| JP | 2000-138270 | 5/2000 |
| JP | 1020010003507 | 1/2001 |
| JP | 2001-159616 | 6/2001 |
| KR | 1020070023979 A | 3/2007 |

* cited by examiner

*Primary Examiner*—Gregory J Toatley, Jr.
*Assistant Examiner*—Amanda H Merlino
(74) *Attorney, Agent, or Firm*—Myers Bigel Sibley Sajovec

(57) ABSTRACT

A method of inspecting a photomask, the method comprising, inspecting at least a portion of the photomask to provide a location of defects having with a first resolution, determining at least one defect region in the location of the defects, the defect region having a defect therein, and imaging the at least one defect region to provide a defect image having a second resolution that is finer than the first resolution.

14 Claims, 6 Drawing Sheets

METHODS, ASSEMBLIES AND SYSTEMS FOR INSPECTING A PHOTOMASK

CROSS REFERENCE TO RELATED APPLICATION

This application claims priority from Korean Patent Application No. 10-2006-0097150 filed on Oct. 2, 2006 in the Korean Intellectual Property Office, the disclosure of which is incorporated herein by reference in its entirety.

BACKGROUND OF THE INVENTION

1. Field of the Invention

The present invention relates to assemblies and systems for inspecting patterns of photomask and methods of performing an inspection process. More particularly, embodiments of the present invention relate to fine resolution inspection of photomasks.

2. Description of the Related Art

A photomask or reticle (hereinafter referred to as a photomask) can be used to transfer an optical pattern image onto a semiconductor substrate when the semiconductor substrate is manufactured. Because patterns of semiconductor devices are formed by using a photomask, forming fine optical patterns on the photomask is desirable.

In order to form fine optical patterns on a photomask, it may also be desirably to inspect the patterns formed on the photomask for defects.

As patterns formed on photomasks become finer, the resolution of systems for inspecting patterns of photomask may be increased to detect defects of the pattern. To obtain high quality resolution, the wavelength of light used in inspecting patterns may also be made relatively small. However, an inspection system with fine resolution typically takes a longer amount of time to inspect a sheet of a photomask. For example, when the length of the side of a unit pixel is reduced by one half (e.g. from 1 μm to 0.5 μm), the amount of time needed to inspect one sheet of a photomask increases by four times.

In comparison with typical systems for manufacturing a semiconductor (including photolithography), systems for manufacturing and inspecting a photomask are more expensive than other systems used for manufacturing a semiconductor. In addition, the process of inspecting a photomask is typically performed in steps after the sheet of a photomask is divided into a number of pixels, which can take a longer time than in other manufacturing process step. If all of the processes of inspecting a photomask are performed by a fine resolution system, more systems for inspecting patterns of a photomask may be provided to keep up with other manufacturing, which increases costs for quality control/review.

Fine resolution inspection systems may increase costs by using additional inspection lines and/or increase labor and other costs for operating and maintaining the inspection line. Accordingly, the introduction of fine resolution systems for inspecting patterns of photomask can be complex and potentially expensive.

SUMMARY OF THE INVENTION

According to embodiments of the invention, methods of inspecting a photomask include: inspecting at least a portion of the photomask to provide a location of defects having with a first resolution; determining at least one defect region in the location of the defects; the defect region having a defect therein; and reviewing the at least one defect region to provide a defect image having a second resolution that is finer than the first resolution.

According to some embodiments of the invention, an assembly for inspecting a photomask includes a first system configured to inspect the photomask to provide a location of defects having a first resolution; and a second system configured to review the location of defects having a second resolution that is finer than the first resolution.

According to some embodiments of the present invention, systems for reviewing patterns of a photomask include a stage configured to mount a photomask thereon; a coordinate analyzing unit configured to receive defect coordinate data; a driving unit configured to drive the stage based on the received defect coordinate data; at least one lens configured to provide image signals according to a shape of patterns of a photomask mounted on the stage; and an image processor configured to receive image signals from the lens and to classify the image data based on a type of defect.

DESCRIPTION OF THE PREFERRED EMBODIMENTS

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

Advantages and features of the present invention and methods of accomplishing the same may be understood more readily by reference to the following detailed description of preferred embodiments and the accompanying drawings. The present invention may, however, be embodied in many different forms and should not be construed as being limited to the embodiments set forth herein. Rather, these embodiments are provided so that this disclosure will be thorough and complete and will fully convey the concept of the invention to those skilled in the art, and the present invention will only be defined by the appended claims. Like reference numerals refer to like elements throughout the specification.

It should be understood that the exemplary drawings may be modified by manufacture techniques and/or tolerances. Embodiments of the present invention are not limited to the accompanying drawings, but may include modifications to be generated according to manufacturing processes. Therefore, regions exemplified in the drawings may have schematic characteristics, and the shape of the regions is an example for specifying regions of elements, not for narrowing the scope of the invention.

Processes for inspecting a photomask according to embodiments of the present invention and systems to be used in the process will be described.

Figure 1:
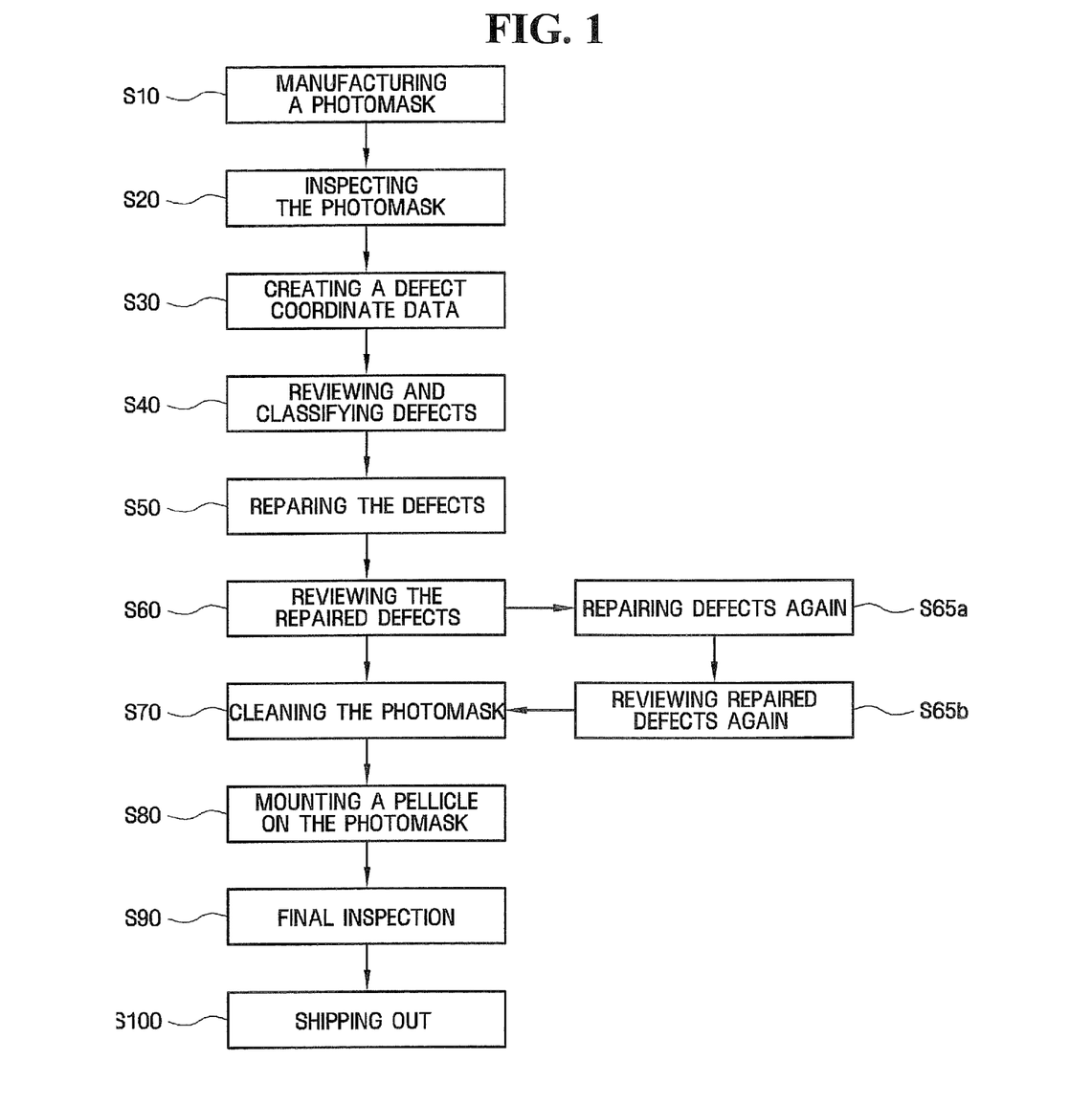
FIG. 1 is a flow chart of operations of inspecting a photomask according to embodiments of the present invention.

Referring to FIG. 1, the processes of inspecting a photomask according to embodiments of the invention includes the following steps. A photomask having patterns on one side using a blank photomask is manufactured (S10). The photomask is inspected to detect defects of the patterns (S20). For example, the photomask can be inspected to provide a location of defects with a first resolution. At least one region of the patterns having a defect therein can be detected. For example, as illustrated in FIG. 1, a coordinate data from the defects of the patterns can be created to indicate coordinates of the defects (S30). The defect(s) can be coordinated to provide a defect image having a second resolution that is finer than the first resolution. Accordingly, a lower resolution can be used to indicate the location of defects on the photomask, and a finer resolution can be used in the selected defect regions to identify the defect and/or to determine what defect repairs should be performed.

As illustrated in FIG. 1, the defects can be reviewed (e.g., at a finer resolution) and/or classified into types on the basis of the created coordinate data (S40). The defects can be repaired, for example, based on the defect classifications (S50). The repaired defects can be reviewed to determine if the repairs are satisfactory (S60). The photomask can be cleaned (S70). A pellicle can be mounted on the photomask (S80). A final inspection can be performed (S90), and the photomask can be shipped out (S100).

If the defects of the patterns are not detected in the inspecting of the patterns (S20), the photomask may proceed directly to the step of cleaning (S70). In some embodiments, if defects are repeatedly detected, when the repaired defects are reviewed (S60) (for example, if there is an error in the repair or if the repair does not fully correct the defect), the defects are repaired again (S65a). The repaired defects may be repaired again (S65b), and the photomask proceeds to be cleaned (S70) if the defects are satisfactorily repaired. However, if defects are still detected when the repaired defects are reviewed (S60), the photomask proceeds can be repaired again (S65a).

Accordingly, a photomask can be inspected and/or repaired by using a lower resolution of a relatively large portion of the photomask to indicate a location of the defect (s). Finer resolution of the identified defect regions can be used to further classify the defects and/or make determinations for performing repairs. The finer resolution may include only selected defect regions; therefore, the amount of time needed to inspect the photomask can be less than if the entire photomask were inspected at the finer resolution.

In particular, in the step of manufacturing a photomask (S110), optical patterns can be formed on the photomask by drawing optical patterns on a blank photomask. A light blocking layer or photoresist is typically formed on a transparent glass substrate by using light or electron beams. The photomask is developed, etched and/or cleaned to complete the formation of the optical patterns. A photomask exposure system is used for drawing optical patterns on the photomask using light or electron beams. A photomask development system is used for developing a photoresist or electron-beam resist formed on the photomask. A photomask etching system is used for selectively removing the light blocking layer using the developed photoresist pattern or electron-beam resist pattern as an etching mask. A resist removing system is used for removing the photoresist pattern or electron-beam resist pattern. A photomask cleaning system is used for cleaning the photomask. Many processes of manufacturing a photomask and systems are well known to those of skill in the art.

The step of inspecting the photomask (S20) can be performed in a photomask pattern inspecting system. The step of inspecting patterns of the photomask (S20) can include optically inspecting whether the optical patterns formed on the photomask are formed in the desired shape that was initially drawn. In this step (S20), after inspecting patterns of the photomask, coordinates of defects or abnormalities are determined and stored based on the results of the inspection. According to embodiments of the present invention, the photomask pattern inspection system inspects the photomask pattern using a first resolution. The first resolution is set based on the efficiency and/or resolution requirements to inspect the photomask and detect defects. For example, if the first resolution is too fine, the ability of inspecting fine defects can be improved, but the amount of time needed to inspect all of the patterns increases. On the other hand, when the resolution is low, the amount of time needed to inspect the all of the patterns decreases, but the ability of inspecting fine defects deteriorates. In this respect, the first resolution can be set properly at an appropriate level. In particular, the first resolution is set so as to be able to inspect noticeable defects. More particularly, with the first resolution, the photomask pattern inspection system can indicate defects, but does not necessarily need to classify the size, shape, and/or kind of defects. The first resolution may be set to find only fine defects, that is, as small as possible, and store the coordinates of the defects. According to some embodiments of the present invention, the size, shape, and kind of detected defect can be classified by imaging defect region at a finer resolution in another system for reviewing and classifying defects. Conventional photomask pattern inspection systems are designed to inspect, classify, and review patterns of a photomask, and consequently, such systems typically need to have a relatively high quality of resolution. However, embodiments of the present invention include a first step at a lower resolution than the conventional system, which results in a relatively shorter time to inspect patterns of a photomask than the conventional systems. A second step can be used in selected defect regions to further classify and/or repair the defects.

In the step of creating coordinate data from defects (S30), the data can be created in the photomask pattern inspection system; otherwise, the data can be created in a main control system for controlling the photomask pattern inspection system by using other methods. To be more specific, in the step of inspecting the photomask to detect defects (S20), the coordinates that are memorized and stored are converted into computer data that can be read in other systems. The defect coordinate data is created in data format that can be read in all of the systems for inspecting patterns of the photomask, reviewing and classifying patterns of the photomask, and repairing patterns of the photomask. Further, the defect coordinate data can be created as computer data in graphic format so as to be displayed on a monitor, such that a control system and/or other monitoring system can read the coordinate data, and an inspector can visually review the defects.

In the step for reviewing and classifying defects (S40), which is performed in a photomask pattern review system, defects of the photomask are reviewed by using defect coordinate data. To be more specific, the photomask pattern review system can display patterns of a photomask which are identified by the defect coordinate data, and an inspector can visually review the defects, and classify the defects. In some embodiments, the photomask pattern review system can automatically classify defects into types e.g., based on defect type data that has been input previously. The examples of types of defects includes spot, pin hole, bridge, dark, clear extension, particle, and etc. Types of defect are well known to those of skill in the art. According to the present embodiment, the photomask pattern review system may have a relatively higher quality of resolution than the photomask pattern inspection system. Unlike the photomask pattern inspection system, the photomask pattern review system does not inspect and/or image the entire pattern of the photomask. The photomask pattern review system detects and/or images a specific location/region on the basis of the coordinate data so as to display the location; therefore, a finer resolution may be used without unnecessarily increasing the amount of time necessary for inspection. In this respect, the resolution may be set to improve the ability of reviewing patterns.

For example, if the photomask pattern inspection system has a first resolution to the level of i-line ($\lambda$=365 nm), the photomask pattern review system may be set to have the resolution at the level of KrF ($\lambda$=248 nm). It should be understood that the resolution of the systems and the wavelength of light used in the systems described herein are illustrative and other resolutions and/or wavelengths of light may be used without departing from the scope of the present invention. For example, if patterns of a photomask become finer, ArF ($\lambda$=193 nm), F2 ($\lambda$=157 nm), EUV ($\lambda$=13.5 nm), FIB (Focused Ion Beam) or SEM (Scanning Electronic Microscope) or the like can be used in the photomask pattern inspection system and the photomask pattern review system.

In addition, the photomask pattern review system can create defect classification coordinate data and/or defect repair coordinate data. These data are used, for example, to determine which method may be used to repair the defects and/or to classify the defects into types. For example, the photomask pattern review system can create defect coordinate data extracted from the data including a portion of the desired pattern to be removed and/or defect coordinate data extracted from the data indicating a portion of the desired pattern to be deposited or the like. The defect classification coordinate data or the defect repair coordinate data may be compatible with defect coordinate data.

The step of repairing defects (S50) may be performed in the photomask pattern repair system. The photomask pattern repair system repairs defects by using, for example, a laser or ion beam, or a diamond blade. The photomask pattern repair system receives the defect classification coordinate data and/or the defect repair coordinate data from the photomask pattern review system to display an image of defect coordinates to be repaired, and repairs patterns e.g. as controlled by an operator. For example, when defects, such as spot, dark, extension, dark bridge, should be removed, a process of removing the defects using laser or ion beam or the like is performed. Otherwise, when defects (such as a pin hole, a clear extension, or a clear bridge) should be deposited, a membrane such as a carbon film is deposited on the defects by using ion beam to repair the defects.

The step of reviewing that defects are repaired (S60) can be performed in the photomask pattern review system according to embodiments of the present invention. To be more specific, whether defects are properly repaired or not can be determined in this step. In this case, defects are primarily reviewed visually; otherwise, the macroscopical inspection is omitted, and defects are reviewed on the basis of defect coordinate data, defect classification coordinate data or defect repair coordinate data. In the step of reviewing the repaired defects, the repaired defects may be displayed on a monitor so as to be reviewed; otherwise, as discussed above with respect to the photomask pattern inspection system, the defects are automatically inspected by using the coordinate data.

If the defects are sufficiently repaired, the photomask proceeds to the step of cleaning (S70). The step of cleaning (S70) can proceed in the photomask cleaning system, and a photomask is cleaned by various dry or wet cleaning methods. Various methods of cleaning a photomask are well known, and a detailed description thereof will thus be omitted.

After the cleaning, a pellicle to protect the patterns can be mounted on the surface of the photomask (S80). The pellicle is typically a transparent green thin film, which protects the patterns of the photomask from outside physical or chemical damages. For example, the pellicle can prevent particle or radical floating in the air from adhering to the surface of patterns of the photomask. Because techniques relating to pellicles are well known, a detailed description thereof will be omitted.

After mounting the pellicle on the surface of the photomask, the photomask is finally inspected (S90). This process can be called a pellicle inspection. In this process, the patterns may be finally inspected one more time, and the pellicle can be inspected to see whether it is mounted well or not.

If in the photomask passes the final inspection (S90), the photomask is inserted in a container and the container is sealed to be shipped out (S100).

If repaired defects do not pass the review (S60) then the defects may be repeatedly repaired, for example, in the photomask pattern repair system (S65a), and the photomask pattern review system reviews the repaired defects again (S65b). After reviewing the defects again, if the photomask passes the review, the step of cleaning (S70) is performed. If again the defects need to be repeatedly repaired, the defects are repaired again (S65a), for example, in the photomask pattern repair system.

Figure 2:
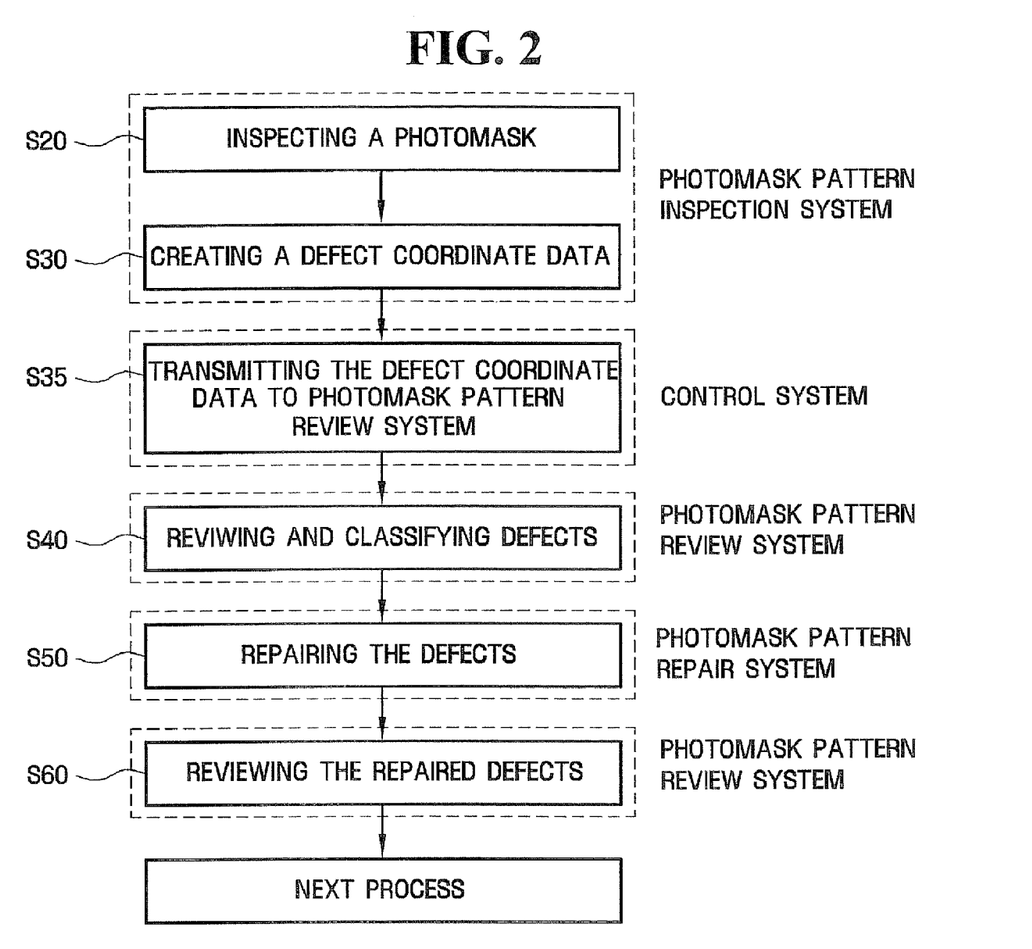
FIG. 2 is a flow chart of operations of inspecting a photomask pattern inspection system, a photomask pattern review system, and a photomask pattern repair system, respectively, according to embodiments of the present invention.

Referring to FIG. 2, the step of inspecting the photomask (S20) and the step of creating the defect coordinate data (S30) are performed in the photomask pattern inspection system. The photomask pattern inspection system will be described below. The defect coordinate data is transmitted to the photomask pattern review system (S35). In some embodiments, the defect coordinate data may be transmitted to the photomask pattern review system continuously. This step may be performed by a controller, for example, a system for controlling some or all of the various systems for each process described herein. Next, the step of reviewing and classifying defects (S40) is performed in the photomask pattern review system based on the defect coordinate data. Next, the step of repairing defects (S50) is performed in the photomask pattern repair system. The step of reviewing the repaired defects (S60) is performed again in the photomask pattern review system. As described above, if the defects that are repaired pass the review, the photomask proceeds to the next process; on the other hand, if the defects do not pass, the process of repairing defects is performed again (S50).

According to the embodiments, the process of inspecting patterns of a photomask, the process of reviewing patterns of a photomask and the process of repairing patterns of a photomask can be separately performed in different systems using two (or more) resolution settings. Therefore, each of the systems can be made according to the desired characteristic of the processes to be performed. As described above, the photomask pattern inspection system can optimize the resolution and inspection speed so as to be able to inspect patterns of the photomask in order to improve productivity. To be more specific, for example, the resolution is set to detect the minimum size of defects that need to be detected. In some embodiments, the photomask pattern inspection system does not use a resolution that can accurately determine and image the defects that are detected, but has the resolution that can recognize portions where defects are generated as defects.

According to some embodiments, the photomask pattern review system for reviewing defect regions may have a finer resolution, for example, a finer resolution than the photomask inspecting system for inspecting a large portion or the entire photomask. In other words, the photomask review system is not used in the process of inspecting patterns of photomask but is used in the process of reviewing patterns in identified defect regions which are located on specific coordinates. That is, because the photomask pattern review system does not perform the process of inspecting a large portion of the photomask, the processing time may be short despite using a fine resolution. On the other hand, the photomask pattern review system can use a resolution that is sufficiently fine to accurately display patterns on the monitor. Therefore, the photomask pattern review system may have a higher quality of resolution than the photomask pattern inspection system.

According to some embodiments, the photomask pattern repair system may include various kinds of system(s). In particular, the system may be a laser system that uses an irradiating laser on the photomask to remove unnecessary defects, or an ion beam system that uses an irradiating ion beam on the photomask to remove unnecessary defects. Other suitable systems can be configured to form a membrane on a region where patterns are not formed, or a system having a diamond blade to physically carve and grind patterns to be removed can be used.

Figure 3:
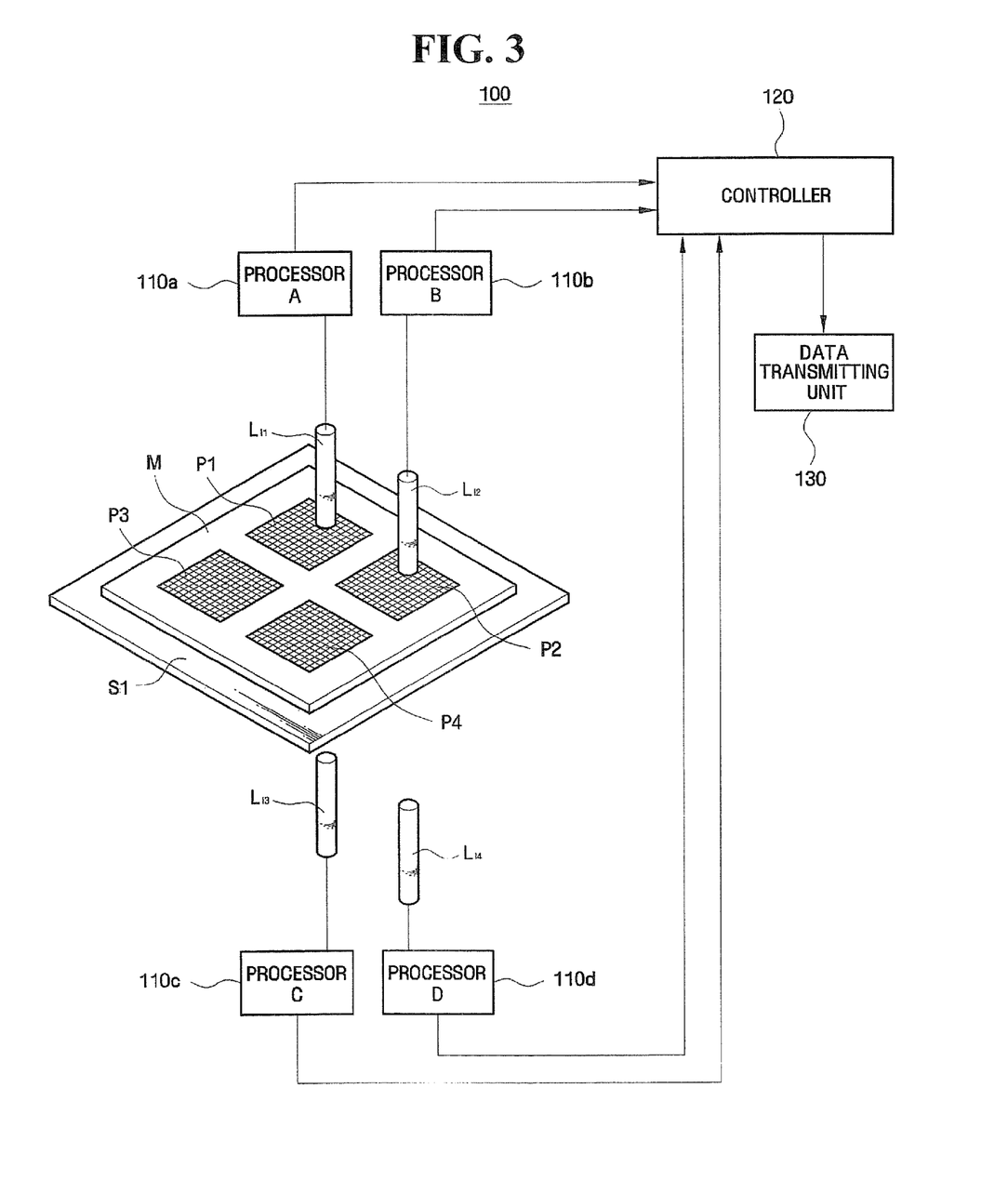
FIG. 3 is a schematic diagram of a photomask pattern inspection system according to embodiments of the present invention.

Referring to FIG. 3, the photomask pattern inspection system (100) according to embodiments of the invention includes a stage S1 on which a photomask M to be inspected is mounted, a plurality of lenses $L_{I1}$, $L_{I2}$, $L_{I3}$, and $L_{I4}$ for inspecting the photomask M mounted on the stage S1, processors 110a, 110b, 110c, and 110d that are electrically connected to the plurality of lenses $L_{I1}$, $L_{I2}$, $L_{I3}$, and $L_{I4}$ and configured to convert optical signals into electrical signals, a controller 120 that receives electrical signals from the processors 110a, 110b, 110c, and 110d to analyze the signals and create a defect coordinate data, and a data transmitting unit 130 for transmitting the defect coordinate data created by the controller 120 to other systems. According to some embodiments, the photomask pattern inspection system (100) uses a first resolution that is sufficiently fine to detect defects in patterns of the photomask without requiring excessively long processing times.

The stage S1 is provided to mount the photomask M thereon, so that the pattern inspection is performed on the photomask, and the stage S1 can move upward/downward and forward/backward by a driving unit (not shown). The stage S1 is formed in a frame shape whose center is hollow, such that the rear side of the photomask M can be inspected.

Two or more of the lenses $L_{I1}$, $L_{I2}$, $L_{I3}$, and $L_{I4}$ are installed at the upper side and lower side of the stage S1, respectively, to inspect the pattern regions P1, P2, P3, and P4 on the photomask M. A method of inspecting the pattern regions P1, P2, P3, P4 of the photomask M by using each of the lenses $L_{I1}$, $L_{I2}$, $L_{I3}$, and $L_{I4}$ will be described below.

The processors 110a, 110b, 110c, and 110d convert optical signals obtained by the lenses $L_{I1}$, $L_{I2}$, $L_{I3}$, and $L_{I4}$ into electrical signals, and transmit the electrical signals to the controller 120.

The controller 120 analyzes the electrical signals transmitted from the processors 110a, 110b, 110c, and 110d and creates defect coordinate data of patterns of a photomask. Further, the controller 120 can create image data, and display the image data on the monitor for comparison.

The data transmitting unit 130 transmits the defect coordinate data which are created by the controller 120 to the other system by using a network. Here, the other system may be a central control system (not shown) for controlling the process of inspecting a photomask or the system for reviewing patterns of selected regions of a photomask.

The photomask pattern inspection system (100) according to the embodiment can perform various methods of inspecting a photomask. To be more specific, first, the method of inspecting patterns of a photomask includes a dark field inspection method and a clear field inspection method. The dark field inspection method is a method of forming patterns of a photomask and inspecting light-blocking patterns forming the patterns of a photomask. In particular, the dark field inspection method can be useful in inspecting defects that are generated on the light-blocking patterns or particles that adhere to the light-blocking patterns. In this method, patterns are inspected by irradiating light on the surface of patterns of a photomask, and then collecting reflected light. In the dark field inspection method, the inspection process is performed by the reflected light, and bright portions on the monitor are the light-blocking patterns. Therefore, in the dark field inspection method, the lenses $L_{I1}$ and $L_{I2}$ itself irradiate light on the surface of the patterns P1, P2, P3, and P4 of a photomask M, and collect reflected light, and thus obtained signals and images are processed to create defect coordinate data. In addition, the rear side of the photomask M may be inspected. In this case, the lenses $L_{I3}$ and $L_{I4}$ located at the lower side of the stage S1 itself irradiate light and collect reflected light, and then information of the light is analyzed so as to process signals and images.

The clear field inspection method is a method for inspecting defects of transparent regions that form patterns of the photomask. In this method, light is irradiated from below the photomask and the light that penetrates the transparent region of the photomask is collected for inspection. Since the light irradiated from the opposite side is collected to perform the inspection process, the bright portion on the monitor is the transparent region. In the clear field inspection method, for example, the lenses $L_{I1}$ and $L_{I2}$ located at the upper side of the photomask M collects the light that is irradiated from the lenses $L_{I3}$ and $L_{I4}$ located at the lower side of the photomask M, so that signals and images are processed to create defect coordinate data. The role of the lenses $L_{I1}$, $L_{I2}$, $L_{I3}$, and $L_{I4}$ may be exchanged. In addition, although the system is illustrated with respect to the lenses $L_{I1}$, $L_{I2}$, $L_{I3}$, and $L_{I4}$, any suitable number of lenses may be used. The rear side opposite to the surface of patterns of a photomask has a technical significance, and can be used in analyzing defects of a transparent substrate.

Any suitable method for inspecting the patterns P1, P2, P3, and P4 can be used. Other methods of inspecting P1, P2, P3, and P4 of the photomask M include a die-to-die inspection method, a mask-to-mask inspection method, a mask-to-database inspection method, etc.

The die-to-die inspection method is an inspection method in which two or more lenses are arranged in different positions from each other, and then optical and electrical signals received from each of the lenses are compared. This method is especially useful in inspecting a photomask for manufacturing a memory semiconductor device. In the case of a memory semiconductor device, since the inside of a cell block is manufactured to have the same shape, lenses are fixed so as to be arranged on the same coordinates inside each of the different cell blocks, then inspection is performed moving the stage S1. FIG. 3 exemplifies the die-to-die inspection method.

The mask-to-mask inspection method is a method in which patterns of two or more sheets of a photomask are compared to each other for inspection. The mask-to-mask inspection method is useful in the case of inspecting a photomask for manufacturing a logic semiconductor device.

The mask-to-database inspection method is a method in which a photomask and database are compared to each other.

Figure 4:
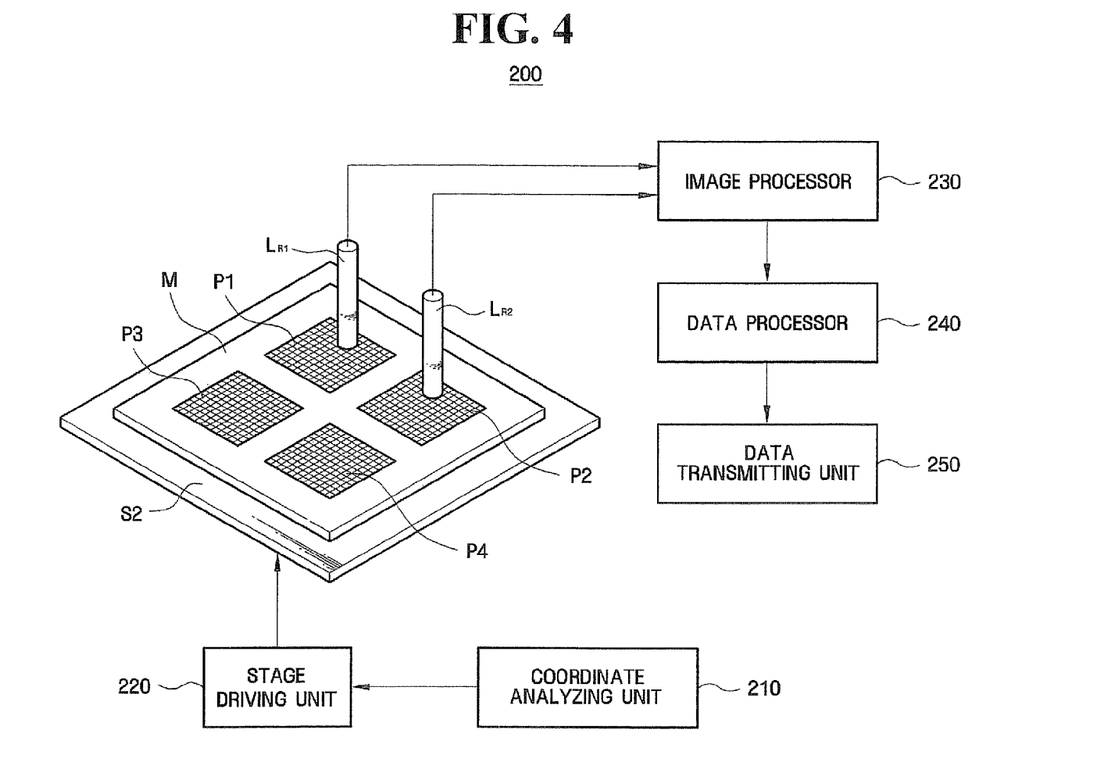
FIG. 4 is a schematic diagram of a photomask pattern review system according to embodiments of the present invention.

Referring to FIG. 4, the photomask pattern review system (200) according to embodiments of the invention includes a stage S2 on which the photomask M is mounted, a coordinate analyzing unit 210 analyzing the transmitted defect coordinate data, a stage driving unit 220 driving the stage with the defect coordinate on the basis of the analyzed coordinate, a plurality of lenses $L_{R1}$ and $L_{R2}$ that is mounted on the stage S2 to review patterns of the photomask M, an image processor 230 that is electrically connected to the plurality of lenses $L_{R1}$ and $L_{R2}$ and converts optical signals into electrical signals to create image data, a data processor 240 that receives information of the patterns of a photomask from the image processor and classifies defects to create repair coordinate data having coordinate information of defects to be repaired, and a data transmitting unit 250 for transmitting the created repair coordinate data.

The coordinate analyzing unit 210 receives defect coordinate data from the central control system or the photomask pattern inspection system and analyzes the defect coordinate data so as to transmit the data to the stage driving unit 220.

The stage driving unit 220 analyzes the signals transmitted from the coordinate analyzing unit 210 to move the stage to the location corresponding to the defect coordinate data. Although the stage driving unit 220 is configured to move the stage, it should be understood that other configurations can be used. For example, a driving unit can be used to move the lenses $L_{R1}$ and $L_{R2}$ to a desired region.

The stage S2 is provided to mount the photomask M thereon, so that the patterns of the photomask are reviewed, and the stage S2 can move upward/downward and forward/backward. The stage S2 is formed in a frame shape whose center is hollow, such that the rear side of the photomask M can be inspected.

The plurality of lenses $L_{R1}$ and $L_{R2}$ transmits optical signals to the image processor 230 to review the defects of the photomask M, by using the same operational principal as the photomask pattern inspection system (100) shown in FIG. 3.

With continued reference to FIG. 4, the image processor 230 analyzes the optical signals transmitted from the lenses $L_{R1}$ and $L_{R2}$, and converts the optical signals into an image, and creates image data so as to display the image data on the monitor.

The data processor 240 creates classification coordinate data or repair coordinate data on the basis of the defects that are classified by the operator. The classification coordinate data is coordinate data that is obtained by classifying the defects detected in the photomask pattern inspection system into classification types. The repair coordinate data is coordinate data having coordinate information of defects based on the photomask pattern repair system or the repair method.

In some embodiments, the photomask pattern review system can create the classification coordinate data and/or the repair coordinate data. For example, various images of defects can be stored in the system in advance, and defects of patterns shown in each coordinate are compared to the stored defects for classification. To be more specific, defects of a photomask can be compared to the various images stored in the system, and classified as the most similar type. This method is a type of image comparison processing and is well known to those of skill in the art.

The data transmitting unit 250 transmits the repair coordinate data to the central control system or the photomask pattern repair system.

Although the photomask pattern review system 200 is illustrated in FIG. 4 with respect to the lenses $L_{R1}$ and $L_{R2}$, it should be understood that any suitable number of lenses can be used.

Figure 5:
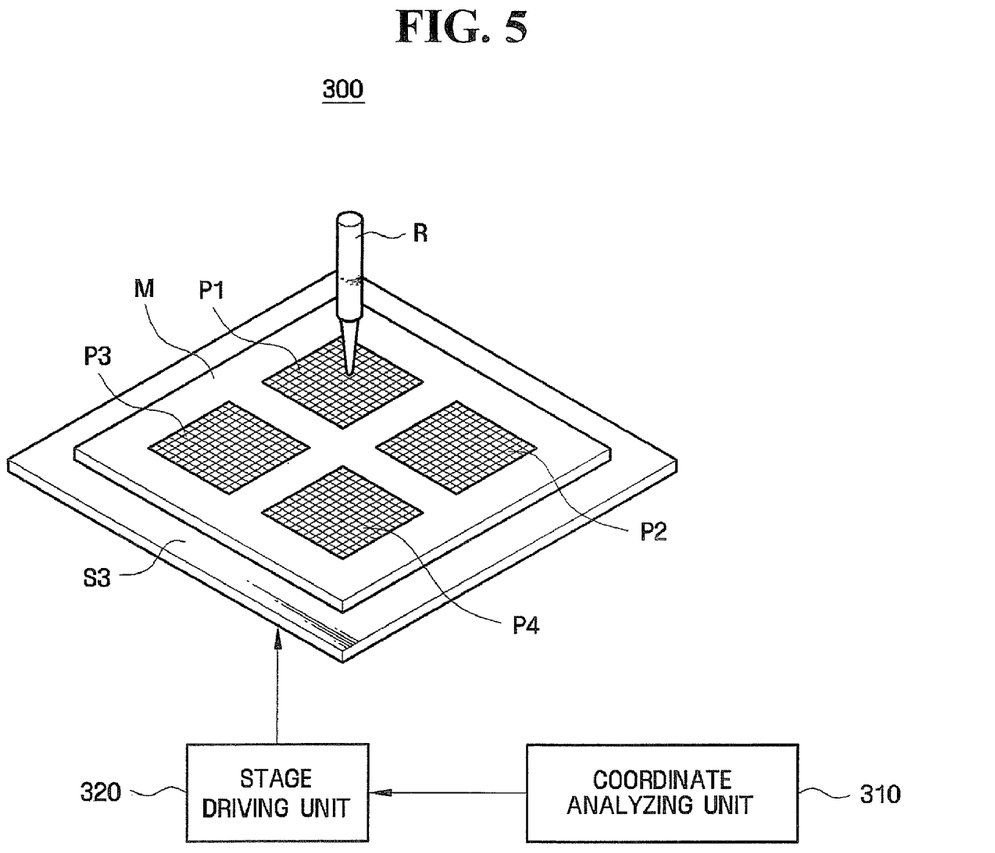
FIG. 5 is a schematic diagram of a photomask pattern repair system according to embodiments of the present invention.

FIG. 5 illustrates a view schematically illustrating the photomask pattern repair system according to an exemplary embodiment of the present invention.

Referring to FIG. 5, a photomask pattern repair system (300) according to embodiments of the invention includes a stage S3 on which the photomask M is mounted, a coordinate analyzing unit 310 for analyzing the transmitted repair coordinate data, a stage driving unit 320 for driving the stage to the coordinate of the defects on the basis of the analyzed coordinate, and a repairing unit R for repairing defects of the photomask M mounted on the stage S3.

The photomask pattern repair system (300) according to embodiments of the invention may include lenses for displaying defects before and after repairs are performed on the monitor.

The repairing unit R can be used in various way according to the repair method. For example, the repairing unit may be a laser gun using an irradiating laser, or an ion gun using an irradiating ion beam, or a diamond blade for physically removing defects.

In the case of using a laser, defects of patterns of a photomask can be removed by irradiating light that is irradiated from the repairing unit R on defects of patterns of a photomask. In the case of an ion beam, defects of patterns of a photomask can be removed by irradiating light that is irradiated from the repairing unit R on defects of patterns of a photomask. In some embodiments, an ion beam that is irradiated from the repairing unit R serves to cover defects of patterns of a photomask. Methods in which defects of patterns of a photomask are removed or covered by using ion beam are well known to those of skill in the art.

In addition, defects of patterns of a photomask can be physically carved or ground by using a fine blade which can be interposed between patterns of a photomask. The blade can be manufactured using the size of tens of nanometers, and formed of diamond materials to enhance intensity.

Figure 6A:
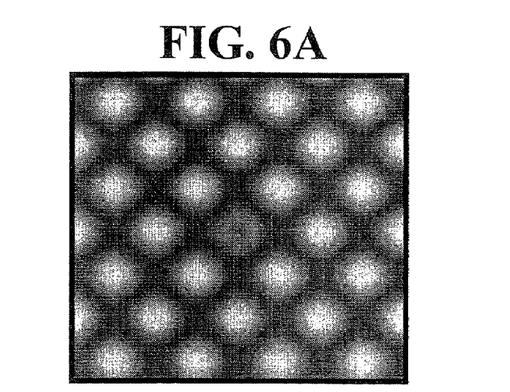
FIGS. 6A and 6B are photographs of patterns of a photomask, which are taken in the photomask pattern inspection system, and the photomask pattern review system.
Figure 6B:
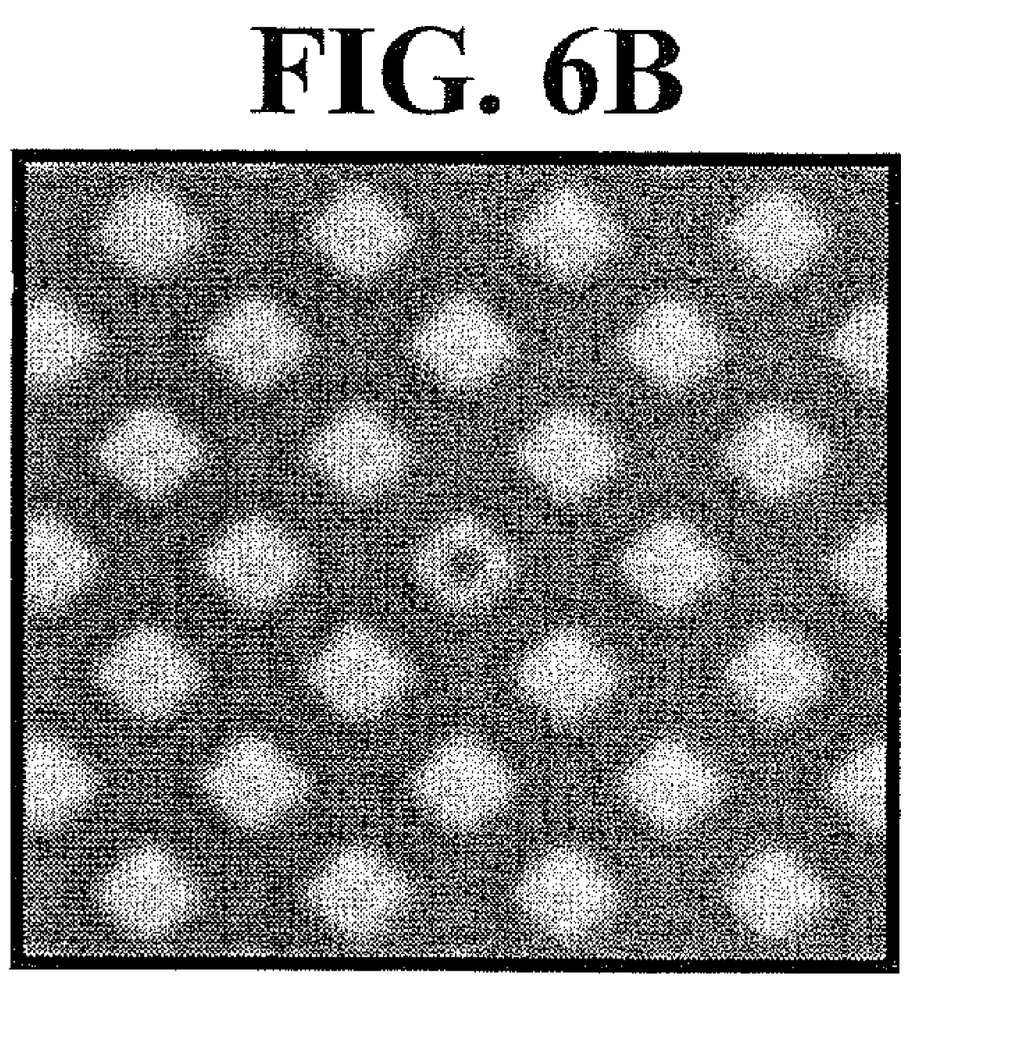

FIG. 6A illustrates an image of the photomask pattern inspection system, and FIG. 6B illustrates an image of the photomask pattern review system. The two images are obtained by taking the same defects of patterns. As shown FIGS. 6A and 6B, the image taken in the photomask pattern review system (FIG. 6B) for imaging a selected defect region has a higher quality of resolution than the image taken in the photomask pattern inspection system (FIG. 6A). That is, as described above, the resolution of the photomask pattern inspection system is set at a resolution that permits the detection of defects while increasing the inspection speed, and the resolution of the photomask pattern review system is set to review the defects at a finer resolution, e.g., for defect classification and/or repair.

Therefore, the systems used in the process of inspecting a photomask according to the embodiments of the present invention can decrease the amount of time necessary for the process of inspecting a photomask according to the related art, thus improving productivity of photomask quality control. Experimentally, as compared to the process in which one photomask pattern inspection system performs inspecting, reviewing and classifying patterns of a photomask and then defects that are repaired, reviewed and classified again, at least 30% of the time necessary for performing the entire process can be saved. To be more specific, about 20% of the process time can be saved in the process of inspecting patterns of a photomask, and about 10% of the process time can be saved in the process of reviewing and classifying patterns of a photomask. Taking into consideration the fact that the time necessary for the process of repairing defects of a photomask and re-reviewing the defects is saved, it is possible to improve the productivity of a photomask inspection and quality control.

As described above, according to embodiments of the invention, the process of inspecting a photomask and the process of repairing defects can be performed accurately and rapidly by using at least two different resolutions, and it is possible to improve the productivity efficiency of photomask manufacturing and/or defect inspection.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed is:

1. A method of inspecting a photomask, the method comprising:

inspecting at least a portion of the photomask to provide a location of defects with a first resolution in a first system;

determining at least one defect region in the location of the defects, the defect region having a defect therein in the first system;

reviewing the at least one defect region to provide a defect image having a second resolution that is finer than the first resolution in a second system that is different from the first system;

repairing the defect in patterns of the photomask in a third system that is different from the first and second systems, wherein the repair is based on the defect image from the second system;

imaging the at least one defect region in the second system to provide a repaired defect image after repairing the defect; and evaluating whether the defect is sufficiently repaired using the repaired defect image from the second system.

2. The method of claim 1, further comprising identifying the defect based on the defect image.

3. The method of claim 2, wherein identifying the defect includes classifying the defect as at least one of a spot defect, a pin hole defect, a bridge defect, a dark defect, a clear extension defect, and a particle defect.

4. The method of claim 2, further comprising providing repair information for repairing the defect based on identifying the defect.

5. The method of claim 2, wherein determining at least one defect region of the photomask includes determining coordinate data identifying a location of the at least one defect region.

6. The method of claim 1, further comprising performing additional repairs if the defect is not sufficiently repaired.

7. The method of claim 1, further comprising displaying the at least one defect region.

8. An assembly for inspecting a photomask, the assembly comprising:
- a first system configured to inspect the photomask to provide a location of defects having a first resolution;
- a second system that is different from the first system, the second system being configured to review the location of defects having a second resolution that is finer than the first resolution; and
- a third system that is different from the first and second systems, the third system being configured to repair the defect in patterns of the photomask based on the repair coordinate data from the second system,
- wherein the second system is configured to image the at least one defect region after the third system repairs the defect to provide a repaired defect image and to evaluate whether the at least one defect region is sufficiently repaired.

9. The assembly of claim 8, wherein the first system comprises:
- a first stage mounting configured to mount a photomask thereon; and
- a first plurality of lenses configured to inspect patterns of the photomask mounted on the first stage.

10. The assembly of claim 9, further comprising a controller configured to create a defect coordinate data.

11. The assembly of claim 8, wherein the second system comprises:
- a second stage configured to mount the photomask thereon;
- a coordinate analyzing unit receiving configured to receive the defect coordinate data from the first system; and
- a second plurality of lenses configured to review the at least one defect region based on the defect coordinate data.

12. The assembly of claim 11, wherein the second system further comprises:
- a stage driving unit configured to drive the second stage on the basis of coordinates that are analyzed by the coordinate analyzing unit;
- an image processor configured to receive optical signals from the second plurality of lenses to form image data; and
- a data processor configured to receive image data from the image processor and to classify defects of patterns of the photomask into types, and creating repair coordinate data having coordinate information of defects to be repaired, wherein the image data is made by a second resolution that is finer than the first resolution.

13. The assembly of claim 12, wherein the data processor is configured to determine repair coordinate data for repairing a defect in the defect region.

14. The assembly of claim 8, wherein the second system is configured to display patterns of the photomask as a visual image on a monitor.

* * * * *